United States Patent
Fahy

(10) Patent No.: US 6,303,388 B1
(45) Date of Patent: *Oct. 16, 2001

(54) PROCESS FOR PREPARING NOVEL ICE-CONTROLLING MOLECULES

(75) Inventor: Gregory M. Fahy, Gaithersburg, MD (US)

(73) Assignee: Organ Recovery Systems, Inc., Charleston, SC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/485,185

(22) Filed: Jun. 7, 1995

Related U.S. Application Data

(63) Continuation-in-part of application No. 08/413,370, filed on Mar. 30, 1995.

(51) Int. Cl.[7] .................................................. G01N 33/543
(52) U.S. Cl. ........................... 436/518; 435/7.1; 435/7.8; 424/184.1; 252/70
(58) Field of Search .......................... 424/184.1; 514/12, 514/21, 2, 8; 435/5, 7.1, 7.8; 239/2.1; 530/350

(56) References Cited

U.S. PATENT DOCUMENTS

| | | | |
|---|---|---|---|
| 4,559,298 | * 12/1985 | Fahy ........................................ | 435/1 |
| 5,118,792 | * 6/1992 | Warren et al. ....................... | 530/350 |
| 5,174,498 | * 12/1992 | Popovitz-Biro et al. ............. | 239/2.1 |
| 5,251,398 | * 10/1993 | Balassa ..................................... | 47/2 |
| 5,336,616 | * 8/1994 | Livesey et al. .................... | 435/240.2 |
| 5,358,931 | * 10/1994 | Rubinsky et al. ...................... | 514/12 |

FOREIGN PATENT DOCUMENTS

WO 94/24413    10/1994    (WO) .
WO 95/01606     1/1995    (WO) .

OTHER PUBLICATIONS

Rotstein et al. "GroupBuild: a fragment based method for de novo drug design". J. med. Chem. vol. 36, pp 1700–1710, 1993.*

Jiang et al. "Soft docking: matching of molecular surfaces cubes". J. Mol. Biol. vol. 219, pp 79–102, 1991.*

Brummell et al. "probing the combining site of an anti carohydrate antibody by saturation mutagenesis: role of the heavy chain CDR3 residues". Biochemistry. vol. 32, pp 1180–1187, 1993.*

Martin et al. "studies of the binding properties of influenza hemagglutinin receptor site mutants". Virology. vol. 241, pp 101–111, 1998.*

Sheridan et al. "using a genetic algorithm to suggest combinatorial libraries". J. Chem. Inf. Comput. Sci., vol. 35, pp 310–320, 1995.*

Gillet et al. "SPROUT: recent developments in the de novo design of molecules". J. Chem. Inf. Comput. Sci., vol. 34, pp 207–217, 1994.*

Rubinsky et al., Hypothermic Protection–A fundamental property of "Antifreeze" proteins. Biochemical and Biophysical Research Communications. 1991 180(2):566–571.*

Ananthanaraynan, V.S. "Antifreeze Proteins: Structural Diversity and Mechanism of Action". Life Chemistry Reports. Harwood Academic Publishers. vol. 7:1–32, 1989.*

Kao et al., "The Relationship between molecular weight and antifreeze polypeptide activity in marine fish". Can, J. Zool. 1986 64:578–582.*

Wu et al., "Enhancement of insect antifreeze protein activity by antibodies". Biochemica et Biophysica Acta. 1991 1076(3):416–420.*

Hruby, V.J. "Conformational and Topographical Considerations in the Design of Biological Active Peptides". Biopolymers. vol. 33:1073–1082, 1993.*

Gupta et al. "Importance of van der Waals Volume in QSAR Studies for Drugs". Journal of Scientific and Industrial Research. vol. 44:189–198, 1985.*

Dean, P. "Recent Advances in Drug Design Methods: Where Will They Lead". BioEssays. vol. 16(9):683–687, 1994.*

Moore, G.J. "Designing peptide mimetics". TiPS. vol. 15:124–129, 1994.*

P. L. Davies et al., "Biochemistry of Fish Antifreeze Proteins", *The FASEB Journal*, vol. 4, May 1990, pp. 2460–2468.

D. S. Yang et al., "Crystal Structure of an Antifreeze Polypeptide and its Mechanistic Implications", *Nature*, vol. 333, May 19, 1988, pp. 232–237.

K. Chou, "Energy–optimized Structure of Antifreeze Protein and Its Binding Mechanism", *J. Mol. Biol.*, vol. 223, 1992, pp. 509–517.

M. Gavish et al., "Ice Nucleation by Alcohols Arranged in Monolayers at the Surface of Water Drops", *Science*, vol. 250, Nov. 16, 1990, pp. 973–975.

(List continued on next page.)

*Primary Examiner*—Donna C. Wortman
(74) *Attorney, Agent, or Firm*—Oliff & Berridge, PLC

(57) ABSTRACT

A dispersal pattern of hydrogen bonding sites on an ice surface is used as a template in a process for the design, selection and manufacture of synthetic ice interface dopants. Ice interface dopants are molecules which when bound to a surface of an ice crystal inhibit the incorporation of additional water molecules into the crystal. The ice interface dopants thus inhibit ice crystal growth, recrystallization, and sublimation. Ice interface dopants can also inhibit heterogenous nucleating agents, and thus postpone or prevent ice nucleation. Exemplary dopant structures are provided that achieve near-perfect ice-bonding efficiency while being thoroughly adaptable to a wide variety of specialized ice-bonding applications. Orbital steering provides for steering lone pair orbitals of ice bonding atoms in the interface dopant to result in an optimal angular alignment with the complementary binding sites on ice.

31 Claims, 10 Drawing Sheets

OTHER PUBLICATIONS

M. Gavish et al., "The Role of Crystal Polarity in α–Amino Acid Crystals for Induced Nucleation of Ice", *Science*, vol. 256, May 8, 1992, pp. 815–818.

C. Knight et al., "Fish Antifreeze Protein and the Freezing and Recrystallization of Ice", *Nature*, vol. 308, Mar. 15, 1984, pp. 295–296.

A. DeVries, "Biological Antifreeze Agents in Coldwater Fishes", *Comp. Biochem. Physiol.*, vol. 73A, No. 4, 1982, pp. 627–640.

G.M. Fahy et al., Abstract No. 213, *Cryobiology*, 28, 584, 1991.

F. Franks et al., "Blood Glycoprotein from Antarctic Fish Possible Conformational Origin of Antifreeze Activity", *Biochimica et Biophysica Acta*, vol. 540, 1978, pp. 346–356.

R. Pain, "Helices of Antifreeze", *Nature*, vol. 333, May 19, 1988, pp. 207–208.

C. Knight et al., "Adsorption to Ice of Fish Antifreeze Glycopeptides 7 and 8", *Biophys. J. Biophysical Society*, vol. 64, Jan. 1993, pp. 252–259.

C. Knight et al., "Adsorption of αHelical Antifreeze Peptides on Specific Ice Crystal Surface Planes", *Biophysical Journal*, vol. 59, Feb. 1991, pp. 409–418.

D. Wen et al., "A Model for Binding of an Antifreeze Polypeptide to Ice", *Biophys. J. Biophysical Society*, vol. 63, Dec. 1992, pp. 1659–1662.

A. DeVries, "Role of Glycopeptides and Peptides in Inhibition of Crystallization of Water in Polar Fishes", *Phil. Trans. R. Soc. Lond.*, vol. B 304, 1984, pp. 575–588.

J. Raymond et al., "Adsorption Inhibition as a Mechanism of Freezing Resistance in Polar Fishes", *Proc. Natl. Acad. Sci. USA*, vol. 74, No. 6, Jun 1977, pp. 2589–2593.

Campbell Soup Research Meeting, Jan. 10, 1991—Gregory Fahy, Ph.D.

Z. Yosida, "Surface Structure of Ice Crystal and Its Equilibrium Form", *Cellular Injury and Resistance in Freezing Organisms*, International Conference on Low Temperature Science, I., Conference on Physics of Snow and Ice (E. Asahina, ed.), The Institute of Low Temperature Science, Sappora, Japan. 1967, p. 2 and 10–11.

F. Franks, "The Physics of Water at Subzero Temperatures", *Biophysics and Biochemistry at Low Temperatures*, Cambridge University Press, New York 1985, p. 21.

R. Evans, "An Introduction to Crystal Chemistry Second Edition", pp. 266–271.

E. Whalley, "Structure Problems of Ice", *Physics of Ice Proceedings of the International Symposium on Physics of Ice*, Munich, Germany, Sep. 9–14, 1968 N. Riehl, B. Bullemer, and H. Engelhardt, eds., 1969, pp. 21–33.

D. Wu et al., "Activation of Antifreeze Proteins from Larvae of the Beetle Dendroides Canadensis", *J. Comp. Physiol B.*, vol. 161, 1991, pp. 279–283.

J. T. Eastman et al., "Antarctic Fishes", *Scientific American*, vol. 254, Nov. 1986, pp. 106–114.

J. Madura et al, "Interactions of the D– and L–Forms of Winter Flounder Antifreeze Peptide with the {201} Planes of Ice", *J. Am. Chem. Soc.*, vol. 116, No. 1, 1994, pp. 417–418.

G. Fahy, "The Role of Nucleation in Cryopreservation", *Biological Ice Nucleation and Its Applications*, Chapter 18, pp. 315–336, 1995.

A. Parody–Morreale et al., "Inhibition of Bacterial Ice Nucleators by Fish Antifreeze Glycoproteins", *Nature*, vol. 333, No. 6175, pp. 782–783, Jun. 1988.

F. Sicheri et al., "Ice–binding Structure and Mechanism of an Antifreeze protein From Winter Flounder", *Nature*, vol. 375, pp. 427–431, Jun. 1995.

Joseph D. Schrag et al., "Primary and Secondary Structure of Antifreeze Peptides From Arctic and Antarctic Zoarcid Fishes", *Biochimica et Biophysica Acta*, vol. 915, pp. 357–370, 1987.

Wei Tang, "Biochemical and Molecular Biological Studies of Antifreeze Proteins form the Insect Tenebrio Molitor", *Dissertation Abstracts International*, vol. 55, No. 2, pp. 307B–308B, Aug. 1994.

James A. Raymond et al., "Inhibition of Growth of Nonbasal Planes in Ice by Fish Antifreezes", *Proc. Natl. Acad. Sci.*, vol. 86, pp. 881–885, Feb. 1989.

Aspen Systems, Inc., "Aircraft De–icing Agent", http://www.aspensystems.com/deicer.html, 1996.

Allen, William, "William Welsh is Fighting Ice with Fire Beetles", *St. Louis Post–Dispatch*, Sep. 6, 1994, News Section, p. 1B.

Welsh, William J., http://macross.uml.edu/umsl_chem/faculty/William.J.Welsh.html.

Kiel, Jacqueline, "Freezing Avoidance in Antarctic Fishes (S–005M)", *Antarctica Sun Times–Online*, Nov. 10, 1996, http://www.asa.org/nsfa/astnov10.htm.

Cloud, Aerosol, and Precipitation Physics and Chemistry, "Fundamental Physics of Ice Formation", http://www.ncar.ucar.edu/archives/asr/ASR94/MMM/capchem.html.

"How Fish Survive the Winter", http://www.cenapad.unicamp.br/CORN . . . UR94/Reports/SPUR_Adam$_{13}$ Report.html.

Terrett, Nick, "Combinatorial Chemistry", *TETNET–The Electronic version of Tetrahedron News*, http://oxford.elsevier.com/tis/tetnet/tetnet1.htm.

MDL Information Systems, Inc., "Combinatorial Chemistry: A Strategy for the Future", Mar. 1995, *Molecular Connection*, 1997, http://www.mdli.com/info/comchem.html.

Jia Zongchao et al., "Structural basis for the binding of a globular antifreeze protein to ice," *Nature*, vol. 384; Nov. 21, 1996, pp. 285–288.

Sicheri, F. et al., "Ice–binding structure and mechanism of an antifreeze protein from winter flounder," *Nature*, vol. 375, 1995, pp. 427–431.

Wen, Dingyi et al., "Structure–Function Relationships in an Antifreeze Polypeptide," *The Journal of Biological Chemistry*, vol. 268, No. 22, 1993, pp. 16401–16405.

Chao, Heman et al., "Structure–function relationship in the globular type III antifreeze protein: Identification of a cluster of surface residues required for binding to ice," *Protein Science*, vol. 3, 1994, pp. 1760–1769.

Gordon, Eric M. et al., "Applications of Combinatorial Technologies to Drug Discovery. 2. Combinatorial Organic Synthesis, Library Screening Strategies, and Future Directions," *Journal of Medicinal Chemistry*, vol. 37, No. 10, 1994, pp. 1385–1401.

Powell, M. J. et al., "Catalytic antibodies—a new direction in enzyme design," *Protein Engineering*, vol. 3, No. 2, 1989, pp. 69–75.

Lerner, Richard A. et al., "Catalytic Antibodies," *Scientific American*, vol. 258, No. 3, 1988, pp. 42–50.

Lehn, Jean–Marie, Supramolecular Chemistry—Scope and Perspectives—Molecules, Supermolecules, and Molecular Devices (Nobel Lecture, *Angewandte Chemie*, vol. 27, No. 1, 1988, pp. 89–112.

Parody–Morreale, Antonio et al., "Inhibition of bacterial ice nucleators by fish antifreeze glycoproteins," *Nature*, vol. 333, 1988, p. 782.

Chemical Abstracts, vol. 105, No. 3, Jul. 21, 1986, Columbus, Ohio, US; Abstract No. 23626.

Chemical Abstracts, vol. 70, No. 23, Jun. 9, 1969, Columbus, Ohio, US; Abstract No. 103995.

* cited by examiner

PROCESS FOR PREPARING NOVEL ICE-CONTROLLING MOLECULES

This application is a Continuation-In-Part of U.S. patent application Ser. No. 08/413,370, filed Mar. 30, 1995, the entire text of which is hereby incorporated by reference.

BACKGROUND OF THE INVENTION

Ice formation is damaging to living systems and food products and may be a nuisance and a hazard to human beings who must cope with snow and ice in their environment. The field of the present invention is the provision of processes for the preparation of specific chemical agents, referred to herein as ice interface dopants (IID), that will effectively reduce ice formation and make ice that does form innocuous to living systems and foodstuffs and less troublesome and hazardous to humans and machinery in the environment.

Referring to FIGS. 1A–B, ice crystallizes in the shape of a hexagonal plate 10. A plane defined by the a axis 12 and the b axis 14 (which is crystallographically identical to the a axis) and perpendicular to the c axis 16 defines a hexagonal cross section called the basal plane 18. The six faces of the hexagon are called prism faces 20. Crystallographically, the basal plane 18 is referred to as the 0001 surface, and the prism face is referred to as the 1$\bar{1}$00 surface or the 1$\bar{1}$20 surface depending on the orientation.

FIGS. 2A–D show that the units of the crystal that give rise to this macroscopic structure are also hexagonal. In FIGS. 2A–D show, following common usage, only the oxygen atoms are represented. The hydrogen atoms lie along the straight lines shown bonding each oxygen atom to its four nearest neighbors.

FIG. 2A shows the basal plane 0001 surface as seen from above. Within each hexagon, three vertices project upward (or forward), and the three intervening vertices project downward (or backward). The upward vertices are separated by 4.5 Å±0.02 Å and are located at a 60° angle with respect to each other. Their fourth bonds extend perpendicularly out of the page toward the viewer. Another spacing at 7.36 Å separates alternate bilayers 21 of oxygen atoms in the lattice, or, viewed differently, separates each oxygen-defined hexagon from an identical hexagon located immediately adjacent to it. FIG. 2B shows views of the crystallographic 1$\bar{1}$00 and 1$\bar{1}$20 prism faces.

Several natural molecules exist that alter the behavior of ice and of water. Antifreeze glycoproteins (AFGPs) and antifreeze proteins or antifreeze peptides (AFPs) produced by several species of fish are believed to adsorb preferentially to the prism face 20 of ice and thus to inhibit ice crystal growth perpendicular to the prism face, i.e, in the direction extending along the basal plane 18 and along the a and b axes 12 and 14.

This capability is sufficient to permit certain fish to live their entire lives at a body temperature about 1° C. below the thermodynamic freezing point of the fishes' body fluids. These fish can ingest and contact ice crystals that might otherwise provide crystal nucleation sites without being invaded by the growth of ice through their supercooled tissues because the AFGPs present in their tissues and body fluids block ice growth despite the presence of supercooling. Insect antifreeze or "thermal hysteresis" proteins (THPs) are even more effective, being active at supercooling levels of 2° C. or more below the thermodynamic freezing point.

The natural "antifreeze" or "thermal hysteresis" proteins found in polar fish and certain terrestrial insects are believed to adsorb to ice by lattice matching (Davies and Hew, FASEB J., 4; 2460–2468, 1990) or by dipolar interactions along certain axes (Yang, Sax, Chakrabartty and Hew, Nature, 333:232–237, 1988).

Antifreeze glycoproteins (AFGPs) and antifreeze proteins or antifreeze peptides (AFPs) found in certain organisms provide natural "proofs of principle" for the concept of novel man-made IIDs. However, natural ice interface doping proteins are not sufficiently active or abundant for most practical applications of interest. Furthermore, a disadvantage of basal plane growth inhibition is that, when supercooling becomes sufficient to overcome ice crystal growth inhibition, growth occurs, by default, predominantly in the direction of the c axis 16, perpendicular to the basal plane 18. This results in the formation of spindle or needle-shaped ice crystals (FIG. 1B) that are more damaging to living cells than normal ice, apparently for mechanical reasons.

Natural IIDs are commercially available only in a very limited quantity and variety. Furthermore, they must have fairly high relative molecular masses (typically at least about 5,000 daltons) to be effective. This tends to make them expensive, and they often require complex interactions with other hard-to-acquire proteins and often require carbohydrate moieties for full effectiveness.

Furthermore, addition of natural fish AFGP to a concentrated solution of cryoprotectant (30–40% v/v DMSO) had minimal effect on ice crystal growth rates below –20 to –40° C. (Fahy, G. M., in Biological Ice Nucleation and its Applications, chapter, 18, pp. 315–336, 1985), thus making questionable its effectiveness for use in organ vitrification for cryopreservation.

Another problem with natural antifreeze proteins is that continuing confusion over their precise mechanisms of action hampers the development of recombinant variants that could be more effective. Recently, Warren and colleagues reported some progress in this direction (U.S. Pat. No. 5,118,792).

The concept of designing specific artificial chemical agents whose purpose is to control the physics of ice was first mentioned by Fahy in *Low Temperature Biotechnology*, McGrath and Diller, eds., ASME, pp.113–146, 1988. The sole mention of this idea was the single statement that "insight into the mechanism of AFP action . . . opens the possibility of designing molecules which may be able to inhibit ice crystal growth in complementary ways, e.g., along different crystallographic planes." However, no method of preparing such molecules was suggested.

Kuo-Chen Chou ("Energy-optimized structure of antifreeze protein and its binding mechanism", J. Mol. Biol., 223:509–517, 1992) mentions an intention to specifically design ice crystal growth inhibitors. However, it is confined to minor modifications of existing antifreeze molecules, and does not envision the present radically different approach of preparing synthetic IIDs de novo.

Based on these observations, it is advantageous to design molecules that can prevent ice crystal growth specifically in the direction of the c axis in accordance with the present invention. When used in combination with an agent acting to block growth in the direction of the basal plane, such that all growth planes would be inhibited rather than only one, such an agent should avoid the lethal drawbacks of the prior art of freezing cells using only basal plane growth inhibitors. Furthermore, since growth in the direction of the c axis, hereinafter "C growth," is the limiting factor for supercooling in the presence of agents that adsorb to the prism face (agents that block growth in the a axis direction, or "A growth"), C growth inhibitors should enhance supercooling considerably over the supercooling achievable with A growth inhibitors alone when used in combination with A growth inhibitors. For this reason, although the principles described herein permit IIDs to be designed to bind to any crystallographic plane of ice desired whatever, or even to non-crystallographic patterns inherent in the ice crystal structure, the specific molecular prototypes described herein have been designed specifically to bind to the basal plane so as to prevent C growth.

A problem with natural antifreeze proteins has been continuing confusion over their precise mechanisms of action. Recently, Sicheri and Yang (Nature 375: 427–431, 1995) described a clear model of how AFPs undergo lattice matching with ice. They indicated that, of 8 AFPs examined, the number of ice-binding atoms ranged from 3 to 10 per AFP and that each AFP formed, on average, ice contacts at between 1 in every 4.8 to 1 in every 15 amino acids present in the molecule (roughly 1 ice bond per 422–1340 daltons of AFP mass). The ice-binding amino acids were threonine, aspartate (asp), asparagine (asn), and lysine. Each binding amino acid formed one bond per amino acid and the bonds were formed by the hydroxyl oxygen of threonine, the amino nitrogen of lysine and of asparagine, and the acid oxygen ($O^-$ or carbonyl 0) of aspartate. For the winter flounder AFP, detailed analysis showed that the lattice matching depended on a planar arrangement of the AFP's bonding groups and on geometrical constraints on the freedom of motion of the matching groups. Bonding took place on the ridges of the 2021 plane (Biophys. J. 63: 1659–1662, 1992; Faraday Discuss. 95: 299–306, 1993; J. Am. Chem. Soc. 116: 417–418, 1994.) More detailed analysis showed that the lattice match between asn and asp oxygen and nitrogen and ice oxygens was imperfect. For one thing, the oxygens in ice associated with these sites were located to the side of each binding atom, not directly underneath. For another, the trigonal planar (sp2) coordination of the hydrogen-bonding groups of asn and asp differ from the tetrahedral (sp3) coordination of oxygens in ice. They concluded that "the underlying hydrogen-bonding interactions are likely to be more liberally defined than previously proposed" by other authors (Biophys. J. 59: 409–418, 1991; Biophys. J. 63: 1659–1662, 1992; Biophys. J. 64: 252–259, 1993).

SUMMARY OF THE INVENTION

The present invention provides processes for preparing ice interface dopants, ice interface dopants prepared thereby, and methods of using them. One process entails determining a distance between hydrogen bonding sites on an ice nucleating body and preparing synthetic molecules having a complementary bonding distance between their own hydrogen bonding sites and the identified sites on the ice nucleating body. Enhanced ice bonding capacity of these molecules is obtained by considering in a design process the novel concept of "orbital steering." Orbital steering refers to the positioning of lone pair electron orbitals in a preferred direction so as to facilitate hydrogen bonding to ice. This is accomplished in part by locking the bonding atoms of the IID into fixed, non-rotating positions by covalently bonding them to at least two other atoms other than hydrogen that form a part of the relatively rigid structure of the IID. Synthetic molecules of the invention may be designed in such a way that they can be both highly active and sufficiently available to be practical to use. A second process is to find IIDs that are essentially antibodies directed against ice. This entails raising actual anti-ice antibodies in animals or by standard "short cut" in vitro cell culture methods, or by searching for complementary protein or nucleic acid IIDs using the methods of combinatorial chemistry.

According to the present invention, IIDs can be prepared that exceed the effectiveness of natural agents. Given that nature has been constrained to using protein, which has limited chemical and structural versatility, and limited evolutionary flexibility, synthetic IIDs as provided herein can vastly exceed the performance of existing natural antifreeze macromolecules, provided proper procedures, as provided by the present invention, are followed. Furthermore, the present invention provides methods of preparing new and optimal protein structures for inhibiting ice crystal formation without regard to existing natural antifreeze proteins or glycoproteins.

The dopant molecules of the present invention can be prepared to adsorb to each surface facet ice presents. Dopant molecules can be prepared to act cooperatively by providing binding sites for other dopant molecules along the edges of the molecule. The invention provides processes for the preparation of molecules that can effectively adsorb to an ice lattice or another ice nucleating surface to preclude ice crystal growth at these ice nucleating surfaces.

The present invention also provides methods for inhibiting the growth of ice in and on various objects, for example, aircraft wings, footwear, pathways, foodstuffs, plants, windows, cables, transplantable tissue including blood tissues, and other objects where control of ice growth is beneficial.

BRIEF DESCRIPTION OF THE DRAWINGS

FIG. 1B shows an ice spicule formation in the presence of a and b axis inhibitors.

DETAILED DESCRIPTION OF PREFERRED EMBODIMENTS

Figure 1A:
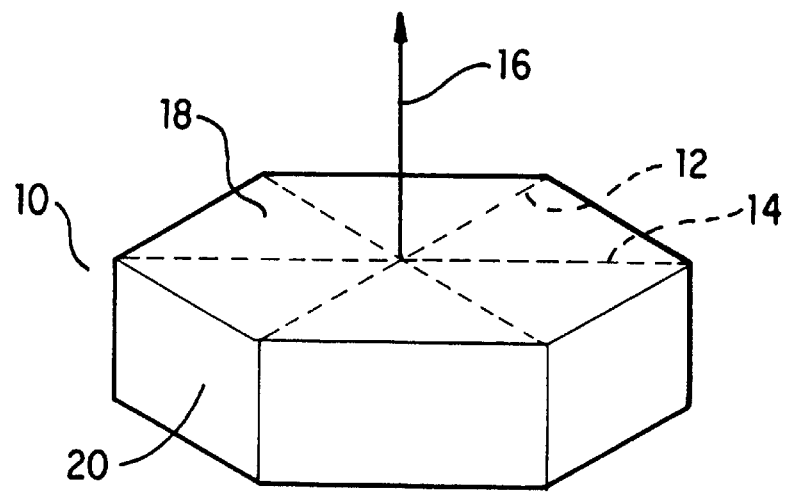
FIGS. 1A–B show the macroscopic prism structure of an ice crystal, including the surface arrangement of the basal plane and the prism faces.

Although the details of preparation of different IID classes as described herein will differ somewhat depending on the specific application, the following primary criteria apply in varying degrees to all categories.

An ice interface as defined herein is the portion of a surface capable of nucleating ice crystal growth. An ice crystal presents several such surfaces and is used throughout the specification as an exemplary ice interface. Heterogeneous nucleators are also considered to possess ice interfaces that may be blocked by the molecules of the instant invention.

The preparation of IIDs by any of the following criteria or combinations thereof will be significantly facilitated by use of adequate computational chemistry packages. Suitable packages include HyperChem (made by Auto Desk, San Francisco, California), ECEPP/2 (see Chou, J. Mol. Biol. 223:509–517, 1992), and Insight II, Discover, and Analysis (made by Biosim Technologies, Incorporated, Parsippany, N.J.), or the direct programs upon which they are based, such as MM2 (Dr. Norman Allinger, University of Georgia). Many less rigorous but still useful programs can also be used. All of these programs are hereby incorporated by reference.

Physical molecular models can also be used to suggest computational molecular models. Physical molecular models allow one to rapidly get a feel for atomic arrangements that accomplish the desired objectives, and they allow for easy visualization of lone pair electron positions in ways not always available using computational models. This is critical because it is the lone pair electrons of oxygen and nitrogen, for example, that bind to hydrogen atoms in the ice crystal lattice.

The following considerations define criteria used for the design and preparation of the various IID molecules:

a. Principles for Balancing the Conflicting Considerations of Molecular Mass, Molecular Mobility, and Molecular Bonding to Ice.

The water molecule is only 18 daltons in mass, and is thus highly mobile in comparison with any structure that may be synthesized for the purpose of inhibiting water adsorption to an existing ice crystal. For the IID to compete maximally with water for access to the advancing ice interface, the molecular mass of the IID should be kept to a minimum. This is particularly true for fast cooling situations. Furthermore, the cost of synthesizing artificial molecules generally goes up as the mass of the molecules becomes larger. Thus, the mass of synthetic IIDs of the present invention is preferably maintained at or under 4500 daltons, and more preferably at or under about 1000–3000 daltons. As disclosed herein, IIDs can be designed with a molecular mass as low as about 100–500 daltons.

By the same token, the effectiveness of a given IID molecule will depend on the area of the ice nucleating interface, for example an ice crystal, that it can cover and on the number of bonds it can form with the ice interface, and both of these will generally decrease as its molecular mass decreases. These factors presumably explain in part why effective natural AFPs are several thousand daltons in mass. Furthermore, excessive molecular mobility on the part of synthetic IIDs could allow high rates of detachment from the ice interface in addition to high rates of attachment to the ice interface.

Yet another factor that will make low mass adverse in some (e.g., biological) though not in other (e.g., industrial) IID applications is the higher osmotic effect of low-mass molecules per unit weight.

To offset the negative effects of lower molecular mass, each IID should satisfy the following criteria.

1. Synthetic IIDs should exceed natural IIDs' ratio of ice bonds to IID mass. According to Chou (J. Mol. Biol. 223:509–517, 1992), the 37 amino acid flounder antifreeze protein forms one bond to ice at every eleventh amino acid. This results in a total of four ice bonds per molecule, or one ice bond for every 819 daltons. Synthetic IIDs should possess a bond to mass ratio of approximately 1 bond per 50 to 500 daltons. Bonding sites should be linearly disposed, that is essentially one dimensional, to minimize nucleation tendency. Alternatively, the ice bonding portion of the molecule should be of limited width or local area for the same reason. Lattice matching over large contiguous areas promotes nucleation (Gavish et al., Science 250:973–975, 1990), but this tendency can be reduced or eliminated by spreading the matching sites apart and/or arranging them in lines.

2. The bonds formed by synthetic IIDs should be at least as strong as bonds formed by natural IIDs, and preferably stronger when nucleation tendencies can be avoided, such as by constructing an essentially linear molecule. Charged groups such as protonated amines or ionized oxygen (as in carboxylic and other acid groups) are preferred, both for strong hydrogen bonding to specific ice lattice sites and for breakdown of local water structure into a non-ice-like form, further discouraging crystal growth. Double-bonded oxygen in carbonyl, sulfoxide, sulfate and phosphate groups is also favored.

The upper limit to bond strength will be determined by chemical toxicity of the bonding group for applications where toxicity is a concern, by the compatibility of the geometry of strong bonding groups in the IID with the geometrical constraints of ice, by unfavorable attraction or repulsion between IIDs at these strongly ice-bonding sites, and by the tendency of particularly strong ice-binding sites to serve as nucleation sites. In certain embodiments, however, the nucleating tendency of very strong ice-bonding sites is not a disadvantage if, at the same time the agent nucleates ice, it also adsorbs to the ice surface to prevent further growth.

3. A good way to form strong bonding without using exotic chemical groups is to rely on the principle of molecular recognition as exemplified, for example, by enzyme-substrate or hormone-receptor affinities. This involves, generally, a 3-dimensional fit between the feature being recognized and the recognizing molecule. Thus, the operating reference mass of the IID is preferably the minimum mass consistent with specific recognition of a particular feature of the ice crystal surface. Total mass may be one or more multiples of this operating reference mass.

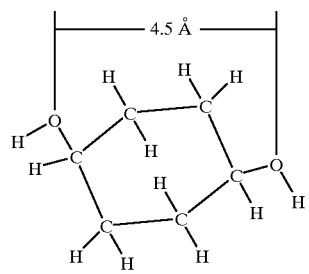

Structure 1

-continued

Structure 2

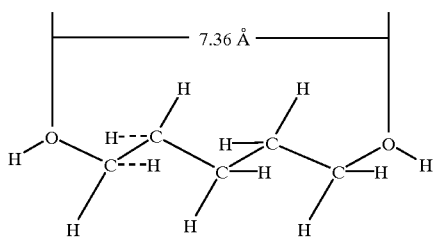

Sample structure 1 and 2 depicts weak (low operating reference mass and therefore low bond number, plus minimal 3-dimensional character) ice recognition molecules with an operating reference mass of approximately 100 daltons (116 and 104 daltons, for structures 1 and 2 respectively). Since each structure has two ice-bonds, the mass to bond ratios are 58 and 52 daltons/bond respectively, compared to 819 for the flounder antifreeze protein.

In structure 1, oxyqens are separated by 4.5 Å, and in structure 2 they are separated by precisely 7.36 Å, an amazingly exact fit to the ice lattice spacing in both cases.

Low atomic number molecules, such as boron and nitrogen are preferred to minimize molecular weight and to maximize mobility and maximize the ratio of ice bonds to IID mass.

b. Cooperativity and Self-assembly.

Cooperativity of bonding to ice inherent in a repeating polymer has the great advantage, of gumming a interactions over large numbers of monomers, maximizing the number of bonds per molecule. An important principle allowing molecules to attain the economies of synthesis and high mobilities associated with lower molecular masses, while at the same time attaining the major advantages of such cooperative binding is to design IIDs to serve as modules in a larger structure. Two examples are a) modules that are independent self-assembling molecules and b) modules that form monomers within a single, polymeric molecule.

For separate molecular modules, side-to-side bonding between edges of the modules, such as hydrogen bonding, can occur when the modules are properly oriented to cooperatively interact with ice. This allows the modules as a population to rapidly self-assemble into an ice-covering surface when an invading ice front becomes available as a template to catalyze this self-assembly process. The mobility of each module allows the module with the most favorable orientation with respect to the intruding ice front to orient itself in the proper manner on the ice front. This slows the growth of the ice front while recruiting other monomers via side-to-side bonding to form an ice-covering film (an "induced fit" process). Laterally-assembling (parallel) rods or strips can form tighter bonds to the ice crystal surface overall than unassociated structures.

An example of a useful type of molecular self-assembly is provided by Ghadiri et al. ("Self-assembling organic nanotubes based on a cyclic peptide architecture", Nature, 366:324–327, 1993, hereby totally incorporated by reference). Ghadiri et al. discloses design of planar cyclic polypeptides that form hydrogen bonds to identical cyclic polypeptides above and below their own plane so as to generate long, self-assembling molecular tubes. The tubes in turn are associated side-to-side to generate structured 3-dimensional arrays. This work involved no recognition of any target molecules other than the cyclic polypeptides. Forming thick 3-dimensional structures is inappropriate for IIDs, which should form more-or-less 2-dimensional or cup-shaped or stair-stepped structures (to maximize the ratio of IID-ice bonds to adsorbed IID mass). However, an essentially 2-dimensional analog of this work, with the further modifications indicated below, would be appropriate for IID preparation.

This approach is preferred in situations where a) there is no limitation on the amount of IID available to cover the ice surface (since this geometry could, by covering the ice surface too intensively at one site, deplete the supply of IID and therefore leave other ice faces uninhibited), and/or b) the IIDs are sufficiently well spaced to avoid the development of nucleator activity that might arise from the IID organizing water molecules into an extensive planar ice-like structure, or c) nucleation is not an issue.

The second modularity approach is modularity within a given molecule. When IIDs must be relatively large, it is generally more economical to create them if they can be designed as condensation products of commonly-available smaller monomers. For example, glycogen is a condensation product of glucose. A modified glucose molecule can be condensed into an IID of arbitrary molecular mass. Natural or modified nucleic acids and natural or modified amino acids can also be polymerized into IIDs of unlimited size at relatively low cost.

The IID should be designed to prevent self-assembly at its ice-bonding side, and preferably also at its complementary side facing away from the ice front. Self assembly on these surfaces will block the functional, i.e. ice inhibiting, sites on the molecules. Steric hindrance and care in positioning polar groups can prevent unwanted self-association.

c. Molecular Shape.

At least some natural AFPs are linear polymers, and at least one appears to lie on or in the crystal as a linear rod (Yang et al., Nature, 333: 232–237, 1988; Chou, J. Mol. Biol. 223:509–517, 1992.) In terms of minimizing the number of atoms needed to attain a given number of hydrogen bonds to ice, however, this arrangement is less preferred than a branched structure, because it bypasses potential bonding sites.

Figure 3:
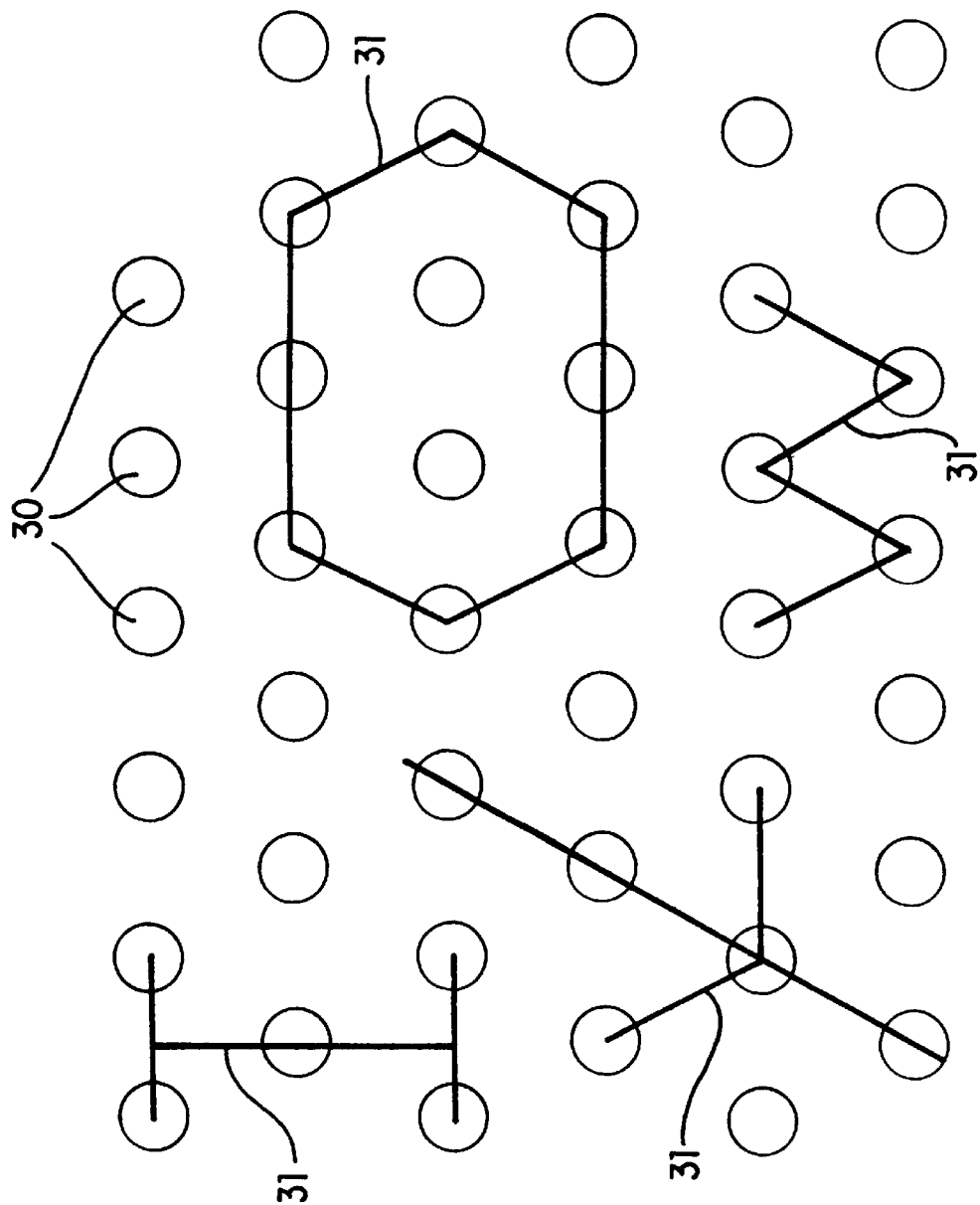
FIG. 3 depicts techniques for maximization of lattice matching using branched or ringed structures that minimize or preclude nucleation tendency.

As shown in FIG. 3, a more preferred approach to achieving tight binding to the forward or upward vertices of ice (other vertices omitted in the Figure), for example, with minimum mass investment is to permit lateral binding, not merely linear binding along a one-dimensional axis, i.e., to design structures 31 that can bind the nearest binding sites, not just binding sites that happen to lie along a particular straight line. This can be achieved by using molecularly branched structures (such as rods with flexibly extending periodic "arms" such as structure 2, or "Y" or "X" shaped molecules), circular (cyclic) structures, or combinations and variations of these forms.

IIDs preferably include steric hindrance features ("bumps" or "standoffs") to avoid or limit self-assembly at the ice-bonding side or the side facing away from ice (the hydrophobic side). Such features may include methyl groups, ethyl groups, crown ether protrusions, etc. Generally standoffs will be hydrophobic or weakly hydrophilic.

d. Amphiphilicity.

Natural IIDs appear to act by placing ice bonding groups (e.g., polar or hydrophilic groups) on one side of the molecule and non-ice bonding groups (e.g., non-polar or hydrophobic groups) on the other, effectively attracting ice on one side and repelling water on the opposite side. This feature generally is preferred in synthetic IIDs, with the cautions indicated above about polar—polar or hydrophobic—hydrophobic interactions on the ice-binding and non-ice-binding faces of the IID, respectively.

e. Lattice Matching.

Lattice matching is fundamental to the binding of IIDs to ice. Lattice matching may involve direct hydrogen bonding to specific ice sites or bonding along electrical resultant vectors on the ice surface (Yang et al., Nature, 333:232–237, 1988). The structure of a normal ice lattice is known. Furthermore, this structure is essentially invariant with temperature, the 4.52 Å spacing decreasing by only 0.04 Å and the 7.36 Å spacing decreasing by only 0.05 Å as temperatures decrease from 0° C. to −196° C. Thus, to a first approximation, lattice matching provides clear design information that can be used to match repeat distances in ice to repeat distances in synthetic IID's. Ice contains several additional lattice matching distances. These include distances of 16.7±0.5 Å for molecules aligning along the $01\bar{1}2$ axis and 6.3±0.4 Å for molecules aligning along the $20\bar{2}1$ ice plane. Bonding sites related by the longer distance form an essentially isosceles triangle of two approximately 16.7 Å sides separated by an approximately 48±2° angle. The approximately 6.3 Å bond length repeats in an essentially linearly disposed pattern.

Complexities are introduced by the mechanics of ice crystal growth in the presence and absence of IIDs. If a flat ice crystal face is presented, the exact positions of the oxygen and hydrogen atoms in that face are, to a first approximation, defined, and a match to these positions can be sought. In a growing crystal, however, newly-added water molecules will be found on the otherwise-flat primary crystal face, potentially interfering with IID adsorption for steric and geometric reasons. Addition of ice to the crystal face will create some disorganization of the crystal face that should be taken into account, and generally ice crystal faces are considered to be molecularly "rough". IIDs are preferably designed to accommodate this situation by "recognizing" steps or bumps on the ice faces and binding to the step or bump sites specifically, or by being step-shaped or concave themselves. The hydrogen bonding sites on step- or bump-recognizing IIDs will bind to ice molecules in two or more lamina of the ice crystal. A means of accomplishing these objectives is described below.

When IIDs 19 are present that induce the growth of spindle-shaped ice crystals 22 in the direction of the c axis 16 (FIG. 1B), one can remedy this "C growth" by adding an IID that binds to the basal plane 18 of ice (the face that faces along the c axis direction 16 perpendicular to the prism face 20). In addition, the side of a spicule may not necessarily resemble well either the normal prism or basal plane structure and an IID designed to match this spicule surface may prevent or help to prevent this type of surface from forming. Therefore, an analysis of the structure of the spicule surface is also advantageous for designing IIDs lattice matching to this unusual surface.

f. Rigidity.

Designed synthetic IIDs are preferably structurally rigid. This is particularly important when fairly large (5 or 6 or more monomers) polymers are created, because free or limited rotation from monomer to monomer rapidly creates a proliferation of different conformational forms of the polymer, most of which will not bind properly to the ice surface. Rigidity allows the IIDs' structure to be well defined, which is both a design advantage and a physical functional advantage in performing lattice matching to a well-defined complementary surface, such as that of an ice crystal.

g. Orbital Steering.

An even more rigorous process for defining a structure of IIDs is the concept of orbital steering. Orbital steering relates to designing bonds into the IID molecule so that lone pair electron orbitals are forced into definite positions.

The usual paradigm of matching oxygens or nitrogens in an AFP with oxygens in ice neglects the fact that a) it may be hydrogen in ice rather than oxygen that is actually being bound, and b) both hydrogen and lone pair electrons of oxygen in ice are located at a 104.5° angle with respect to each other.

Figure 5:
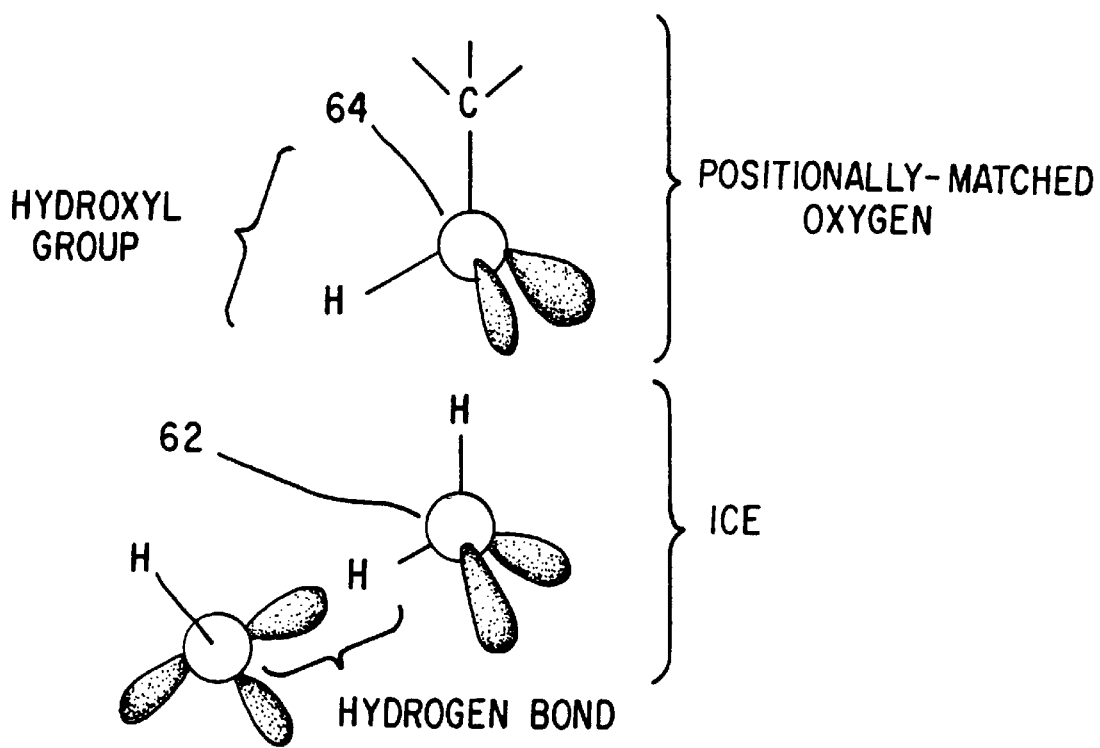
FIG. 5 shows an ice lattice structure with a dopant molecule attached.
Figure 6:
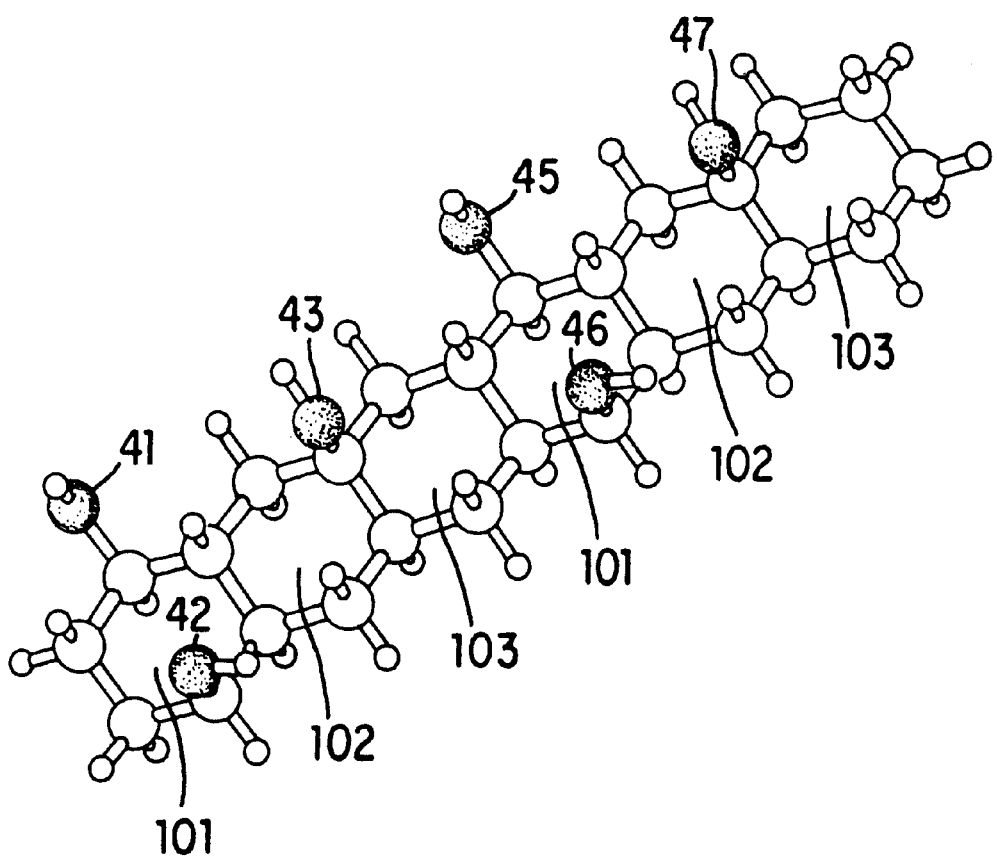
FIG. 6 shows the relationship between the lone pair electrons of a hydroxyl group and the bonding sites in ice that exists when the oxygen of the hydroxyl group is oriented directly above an oxygen atom in ice.

FIG. 5 shows one possible effect of matching oxygen positions in a molecule with oxygens in ice lattice sites as has been commonly related in the literature to be an ideal strategy for ice bonding. The example shown uses the basal plane as the bonding surface for the IID. The oxygen positions 62 and 64 are superimposable, but the bonding is weakened by failure of the orbitals in ice 62 to align properly with the orbitals of the binding molecule 64 to permit hydrogen bonding. "Orbital steering" provides an exact orbital orientation which should be more effective for binding to the ice lattice than just a local electron density increase designed into "non-orbitally steered" IID molecules.

Similar problems are found in natural AFPs. Orbitals are not aligned properly for proper hydrogen bonding. Despite this, natural AFPs are effective, but are not as effective as artificial IIDs that can be designed to achieve precise orbital alignment. The positioning of the bonding atom in the ring forces the lone pair electron orbitals to assume specific positions and these specific and predictable positions can be arranged to be parallel to each other and spaced appropriately for bonding to appropriate atoms in ice.

In addition to oxygen, other elements having lone pair electron orbitals can be used in much the same way as oxygen but to arrive at slightly different architectures.

For example, nitrogen can serve as a vertex separating two rings, and unlike oxygen, should project a lone pair above the plane of a graphitic surface.

Chirality of the bonds is important. If an alternate enantiomorph is used, the lone pair orbital electrons will not be optimally oriented.

h. Surface Characteristics Acceptable Void Areas.

Figure 1B:
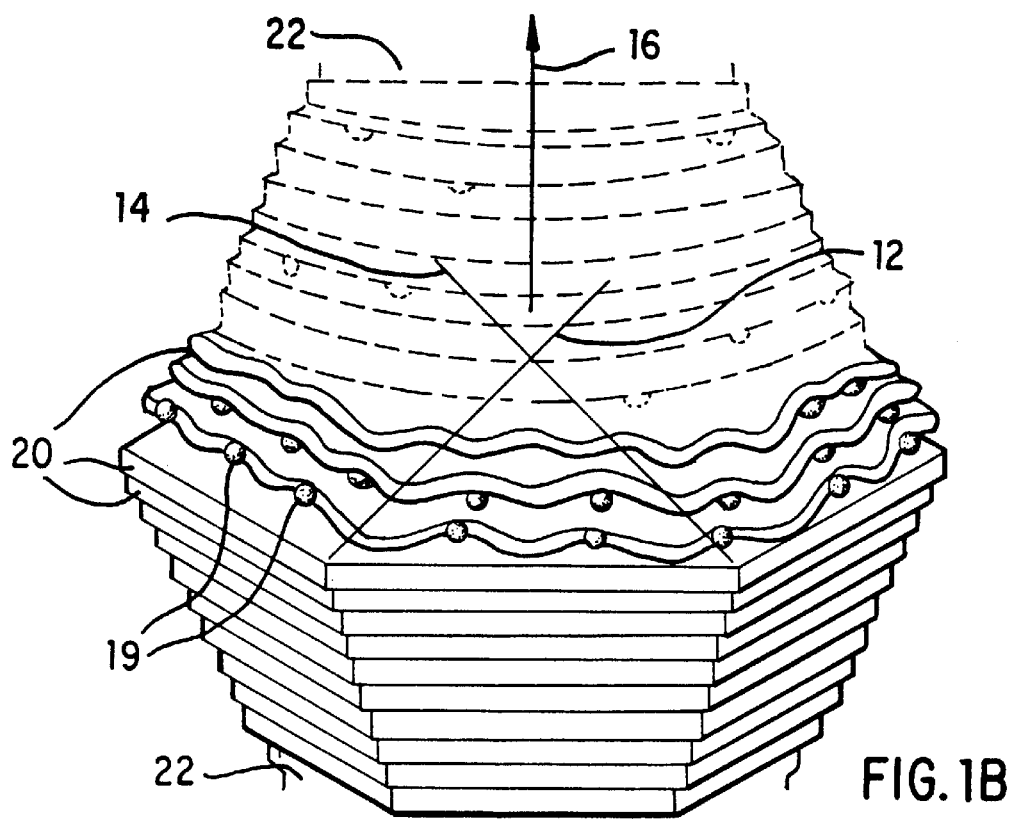
Figure 2A:
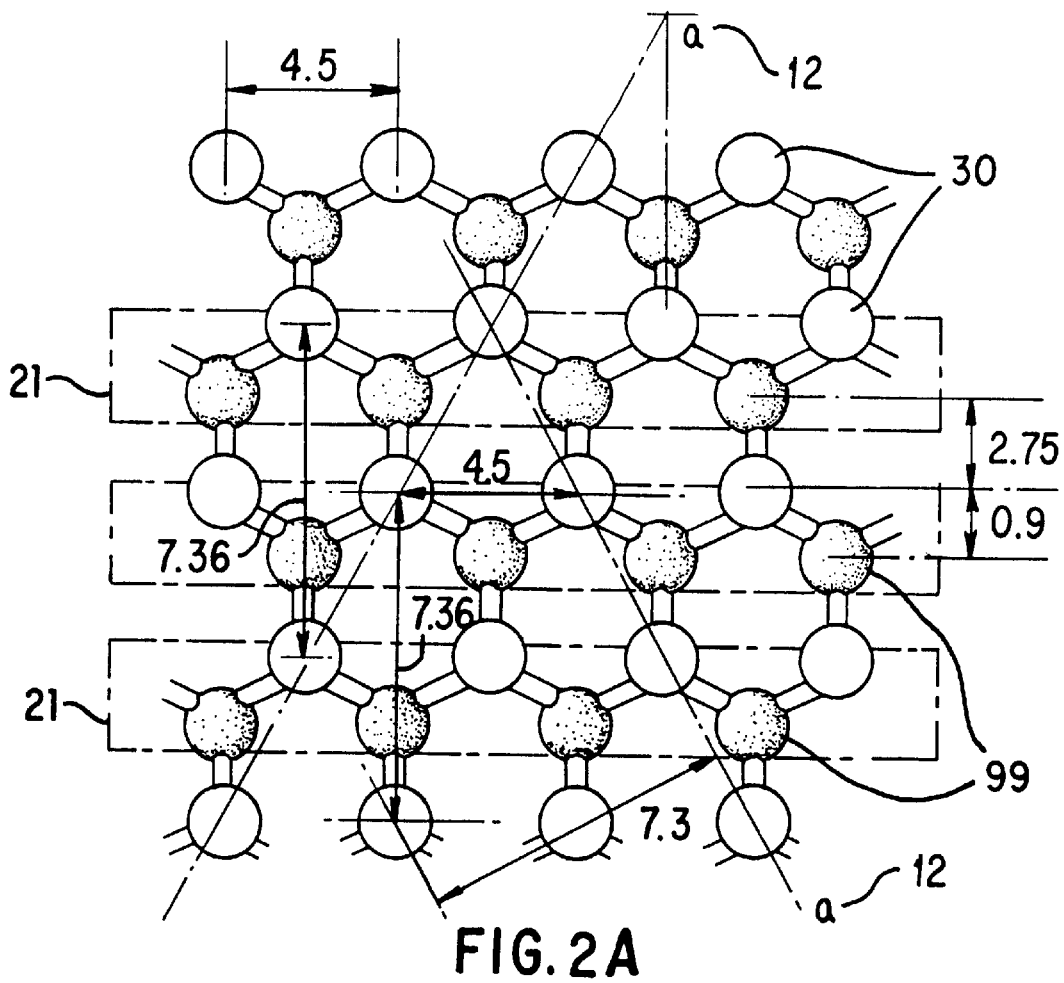
FIGS. 2A–D show the lattice structure of the basal plane 0001 (FIG. 2A) and the prism faces (FIG. 2B) of an ice crystal.
Figure 2B:
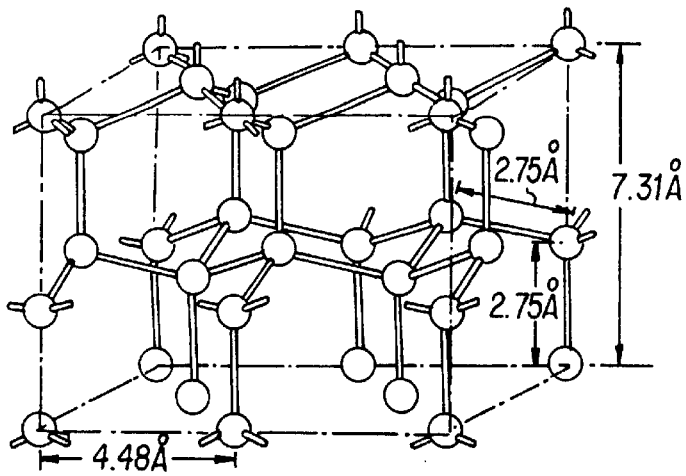
Figure 2C:
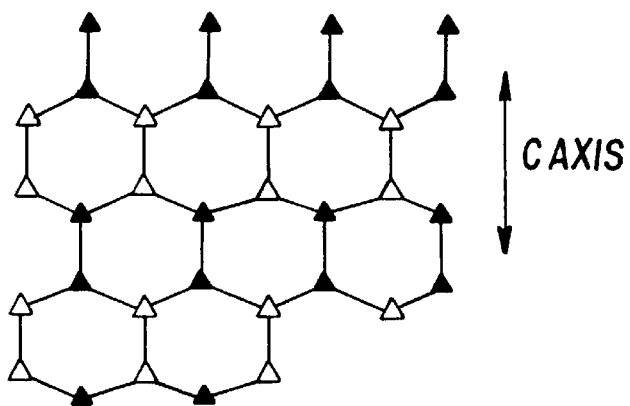
Figure 2D:
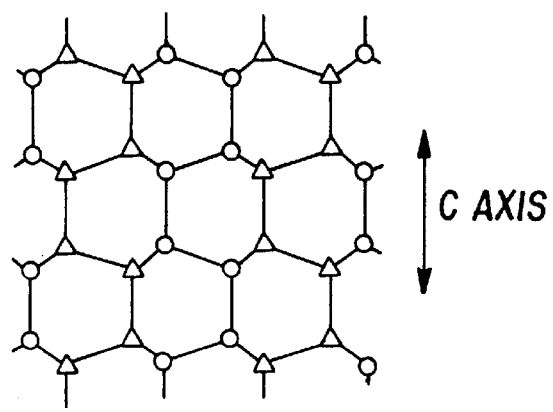

As illustrated in FIG. 1B, natural IIDs 19 cover only a small fraction of the ice crystal surface, yet are effective. This is accomplished because growth inhibition is not purely a matter of steric interference with the approach of water molecules to and their adsorption on the ice surface. Rather, it is also a matter of the lack of lateral bonding sites for an adsorbed water molecule to provide stabilizing forces to prevent spontaneous loss of the adsorbed water molecule back into the surrounding solution, in other words, a matter of the surface energy of ice (the Kelvin effect; see Mazur, Ann. N.Y. Acad. of Sci., 125:658–676, 1965). Adsorption of IIDs indirectly creates an increase in ice surface energy between IID adsorption sites, thus producing an ice-retarding effect that extends very many molecular diameters over the ice surface beyond the IID adsorption site itself as indicated in FIG. 1B.

The value of this effect decreases as the extent of supercooling of the liquid medium increases and the driving force for crystallization thus increases to overcome the higher ice surface energy barrier to crystal growth. IIDs therefore should be designed to cover sufficient surface to be appropriate for the extent of supercooling that is important for the particular application at hand. Thus appropriate void spaces for IIDs used for protecting orange groves may be larger than appropriate void spaces used for food freezing and the latter void spaces may exceed those that are appropriate for biological cryopreservation.

The Kelvin equation describes the freezing point depression caused by forcing ice to assume a highly curved (high energy) shape in order to propagate through an aperture. This equation is also applicable to the freezing point depression caused by restricting ice surface area between both natural AFPs/AFGPs (Wilson, Cryo-Letters; 14:31–36, 1993) and synthetic IID molecules. Thus, in designing a circular IID, for example, this relationship establishes the diameter of the IID loop that will protect against ice crystal growth through the loop at a given level of bulk solution supercooling. If extreme extents of supercooling are required (as in organ vitrification), complete inhibition of crystal growth may not be feasible without complete coating of ice nuclei, but complete inhibition may be unnecessary if crystal growth is sufficiently slow. In the latter consideration, the smaller the loop diameter the slower the crystal growth will be, until the diameter becomes small enough to possibly induce ice nucleation activity.

i. Template-mediated Synthesis of IIDs.

Ice nucleating agents (INAs) are the functional opposites of THPs. They induce ice crystal nucleation rather than ice growth inhibition. Both THPs and INAs clearly must have a structural relationship to ice. Whereas THPs bind to ice, they do not resemble ice. INAs, because they create ice, are considered to more closely "resemble" ice, either structurally (as in AgI, mica or cholesterol crystals) or in terms of having a surface energy that is similar to that of ice, as might be the case for *Pseudomonas syringae* nucleating sites. Parody-Morreale et al. (*Nature,* 333:782–783, 1988) showed that fish antifreeze glycoproteins inhibited nucleation by bacterial ice nucleators, suggesting that the antifreeze molecules bind to the nucleators due to the ice-like structure of the nucleators.

One existing technology for making molecules that bind to particular structures found in biology is to inject these structures into an animal. The animal will make antibodies to many foreign substances, the antibodies having a close structural complementarity to these substances. However, it is impossible to form antibodies to ice simply by injecting ice into an animal. This obstacle may be overcome to allow synthesis of antibody IIDs based on the recognition that (a) an antibody that binds to a bacterial ice nucleator or to another known ice nucleating substance may also bind to ice, and (b) that an antibody that binds to ice may function as an IID to block ice crystal growth, and may do so more effectively than natural AFPs.

A method of preparing IIDs by this route is to select an appropriate nucleator, raise antibodies to it, such as by methods known in the immunology art, and screen the antibodies for effectiveness for inhibiting ice crystal growth and/or binding to ice.

Exemplary nucleators include *P. syringae* nucleator fragments (fragments to allow exposure of the nucleator site to the antibody), previously synthesized IIDs, IIDs attached to proteins or associated with other adjuvants to make them more immunogenic, THPs/AFPs, cross linked modified $C_3OH_{61}OH$ alkane alcohol chains arranged with 4.5 Å spacing between head groups or tails (Gavish et al., Science, 250:973–975, 1990), cross linked crystals of α-amino-octanoic acid, 1-methionine, d,l-tyrosine, or d,l-alanine and similar species (Gavish et al., Science, 256:815–818, 1992), and previously formed anti-ice antibody fragments.

Screening for crystal growth inhibition and for ice binding activity can be performed as a matter of routine experimentation. Routine assays for the inhibition of ice crystal growth are known (for example, see Knight, DeVries, and Oolman, Nature 308:295–296, 1984). One assay for antibody binding to ice is to label (radioactively, fluorescently, enzymatically, and if necessary, antigenically or otherwise) the antibodies and measure the partitioning of label from the liquid phase to the ice phase when low concentrations of antibody are added to a mixture of ice and solution at a static temperature when the ice is at its thermodynamic freezing point. Another assay for binding activity is the ice crystal growth habit assay (Knight et al., Nature 308:295–296, 1984).

j. Synthesis of IIDs through Combinatorial Chemistry.

The field of combinatorial chemistry uses transcription systems to generate large numbers of protein or RNA variants that are then screened for the desired activity (Alper, Science 264:1399–1401; Kenan, Tsai, and Keene, T.I.B.S., 19:57–64, 1994). This extremely powerful approach is direct, in contrast to the indirect antibody approach, which requires an artificial ice surrogate.

If the desired activity is binding to ice, the best products (proteins or even nucleic acids, or unnatural variations [Fahy, Clin. Chem. 39:2011–2016, 1993] of either) for ice binding can be determined by screening the products made by the combinatorial approach for ice adsorption to a crystallographic plane of interest. For example, finely divided ice may be used as a device for concentrating good ice binders from an initial mix of candidates by repetitively segregating the ice fraction (for example, by lifting or filtering the ice out of the solution) after binding, then melting the ice, and checking the melt for enrichment of selected molecules in the new candidate solution formed.

EXAMPLES

A Generic IID.

As noted above, the 37-amino acid flounder antifreeze protein forms as few as one hydrogen bond per eleven amino acid residues, or a ratio of one bond per 819 daltons or so of AFP. FIG. 6 shows a synthetic IID 3 (Structure 3) designed to have one bond per 75 daltons of IID. This IID was constructed and dimensions were determined using HyperChem, a computational chemistry software package that typifies software available to facilitate the preparation of novel IIDs given the principles described here.

Bonding sites are represented by the oxygen atoms 41–43 and 45–47. Structure 3 consists of three monomer rings 101, 102 and 103 that act as a supermodule that is repeated once. The spacing of oxygens across the width of the strip is precisely 4.50 Å (oxygens 41 to 42 and 45 to 46), and the nearest oxygen spacing along one edge of the strip is 4.55 Å, a negligible difference from the 4.52 Å spacing of ice oxygens. Furthermore, the spacing between oxygens 41 and 45, and between oxygens 42 and 46, is 7.54 Å, a close match to the 7.36 Å spacing of ice oxygens. The spacings across the strip (41 to 42 and 45 to 46) do not resemble the spacings in sugar molecules observed by DeVries, and the spacings along the strip edges also resemble no structure ever before contemplated. The combination of the axial spacings, e.g., oxygen 41 to 43 and 41 to 45, with the lateral spacings, e.g., oxygens 41 to 42, so as to match the triangular site distribution pattern of ice, similarly represents a previously-unknown structure and motif.

This design illustrates the internal modularity of the IID (rings 101–103), the planar (and by implication the potentially ring-shaped nature) of the IID, the positioning of polar groups exclusively on one side of the amphiphilic molecule, the use of at least moderate structural rigidity to ensure faithful positioning of bonding sites, the minimization of IID mass and local area, and the attainment of considerably more ice bonding per unit mass than is achieved by natural IIDs. The potential for inserting lateral polar groups for side-to-side hydrogen bonding into cooperative arrays is also evident.

Figure 4:
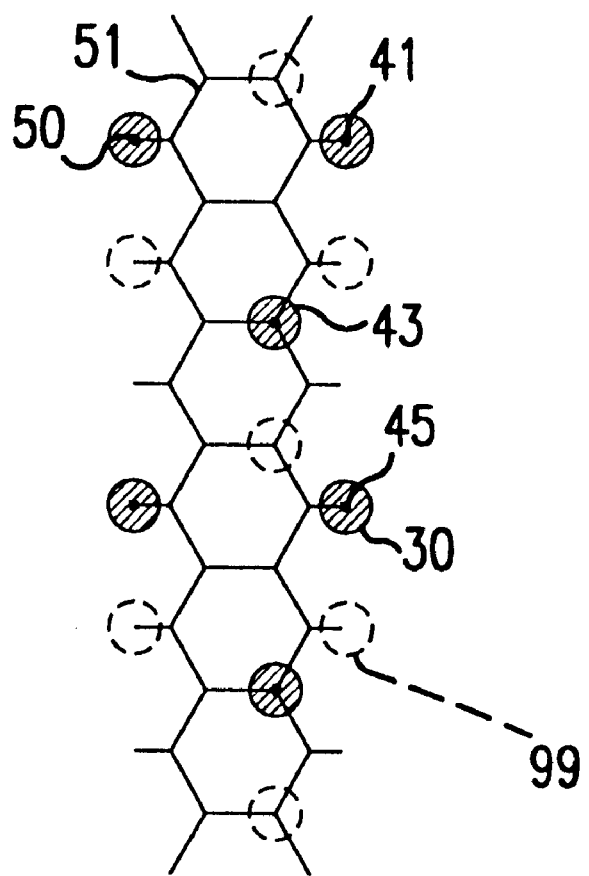
FIG. 4 shows an adaptable dopant molecule with hydrogen bonding sites for bonding to an ice nucleating body.

In FIG. 4, oxygen atoms in the uppermost layer of the ice crystal 0001 basal plane surface 18, are shown as unbroken circles. Shaded circles represent bonded ice lattice sites. In FIG. 5, 51 represents structure 3 that has been rotated so as to face the basal plane surface to permit hydrogen bonding. For orientation some oxygen atoms of the IID (41, 43, 45) have been identified using the same numbering shown in FIG. 4. The diagram discloses that all available sites 30 are in fact bonded by the IID.

FIG. 4 emphasizes the remarkable coincidence between the spacing of strategically-located hydroxyls on a graphitic "molecular pegboard" backbone and the 4.5 Å and 7.4 Å spacing of forward-projecting oxygen atoms of ice. Of the 6 oxygen atoms 41–43 and 45–47 (shown as the small black dots 50), all 6 are directly positioned over forward oxygen atoms in the ice lattice shown as shaded circles, and the number of bonds/dalton for structure 3 is over 10 times the number identified for one antifreeze protein by Chou. In fact, the ability of the IID 3 to bond to every single vertex 30 in its path indicates that it may represent the structurally most perfect IID motif that can be created for the unmodified basal plane.

Structure 3 exemplifies one preferred class of dopant of the present invention that prevents ice crystal growth specifically in the direction of the c axis 16. When used in combination with an agent acting to block growth in the direction of the basal plane 18, such that all growth planes would be inhibited rather than only one, such an agent should avoid the lethal drawbacks of freezing cells that attend using only basal plane growth inhibitors. Furthermore, since growth in the direction of the c axis 16 ("C growth") is the limiting factor for supercooling in the presence of agents that adsorb to the prism face 20 (agents that block growth in the a axis direction, or "A growth"), C growth inhibitors used in combination with A growth inhibitors should enhance supercooling considerably over the supercooling achievable with A growth inhibitors alone.

AFPs plus a c axis selective IID should also reduce freezing injury by preventing ice crystals from growing to appreciable sizes during cooling as well as by preventing ice crystals from coalescing during warming, a process variously referred to as grain growth, recrystallization, or Ostwald ripening. Excessive growth of ice crystals is thought to be the primary means by which freezing damages the delicate extracellular structures present in organized tissues and organs and leads to the failure of these tissues and organs after thawing. Thus, the invention provides superlative control of ice crystal size and stability during cooling and warming, and provides an alternative approach to vitrification for the cryopreservation of complex systems, achievable with dramatically less technical complexity.

The structure 3 has the further advantage of being finely adjustable to any desired ice crystal morphology by virtue of the fact that the graphitic backbone's tetrahedral arrangement is clearly capable of following the ice lattice's tetrahedral arrangement. Carbon hexagons can be built out from the "strip-like" structure 3 shown into the surrounding plane in any manner desired, similar to patterns shown in FIG. 3.

(FIG. 4 reveals that the geometry of the IID 3 is such that it effectively possesses branching character in that Structure 3 most resembles the "I" shape of FIG. 3.) Furthermore, carbon hexagons can be built upwards or downwards from the parent plane as well using a similar geometrical construction perpendicular to the plane.

Evidently, the ability to create an extended matching pattern between structures like structure 3 and ice has not heretofore been recognized. DeVries noted one sugar OH—OH spacing of 4.5 Å in isolation in antifreeze glycoproteins containing the N-acetylgalactosamine residue on a repeating Ala-Ala-Thr structure (DeVries, Comp. Biochem., 73A:627–640, 1982), but this sugar spacing resulted from a different, more limited geometry not suggestive of artificial IIDs like the IID 3.

Orbitally steered IIDs.

Figure 7:
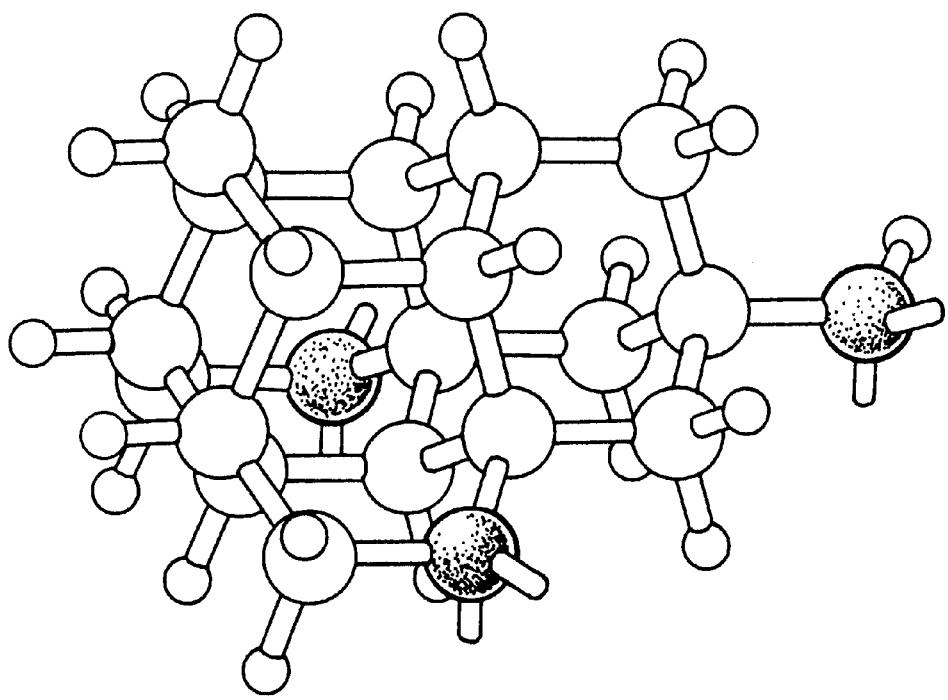
FIG. 7 shows the steered orbitals of an artificial IID (IB2) arranged in such a way that they form an almost perfect match to the hydrogens of the basal plane of ice.
Figure 8:
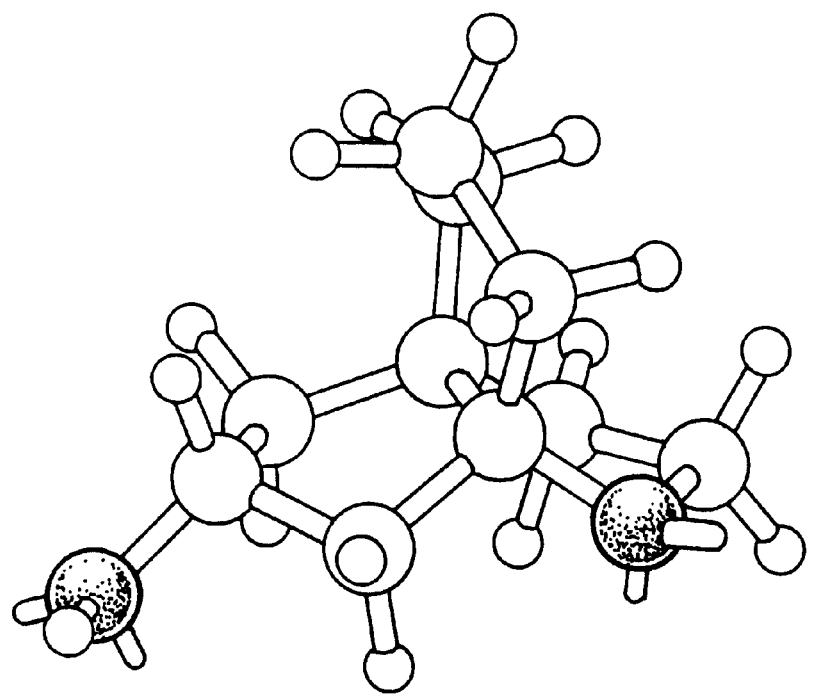
FIG. 8 shows an example of a partly steered artificial IID (IB3) in which one oxygen is steered and the other is located in a permissive position for rotation into the correct orientation.
Figure 9:
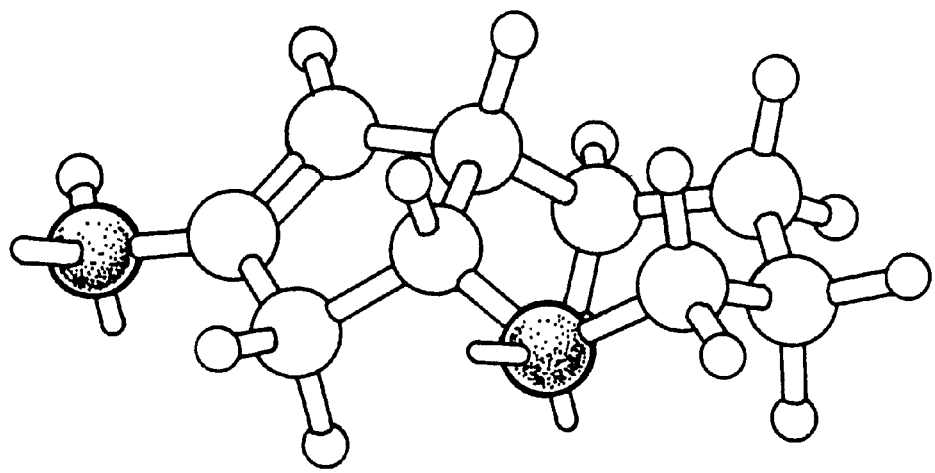
FIG. 9 shows a second example of a mixed steered and unsteered IID employing the same principle as that employed in IB3 but using a different physical embodiment.

FIG. 7 shows a molecule with three oxygen atoms bound in such a way so as to orient the lone pair electrons from each oxygen molecule into definite positions. A variation of this theme is shown in FIGS. 8 and 9 wherein at least one oxygen atom is "locked" and one or more of the remaining oxygen atoms are positioned to allow their orbitals or bound hydrogens to rotate into a parallel alignment to that of the locked oxygen atom.

This approach combines such "locked" atoms with atoms that are free to rotate about a single bond but whose rotating orbitals are capable of assuming positions that are approximately parallel to and spaced appropriately from "steered" orbitals so as to allow bonding to atoms in ice.

FIG. 7 represents a prototype orbitally-steered IID that achieves the goal of bonding all three vertices of an ice oxygen hexagon when all such vertices terminate in a hydrogen atom. The lone pair electrons 71, 72 and 73 of the oxygens 74, 75 and 77 are shown projecting directly downward from the IID for alignment with great fidelity with the ice hydrogen atoms, to form three strong hydrogen bonds. The positions of two of these orbitals 71 and 72 are not freely movable and are therefore correctly aligned for ice bonding at all times. This arrangement is referred to as "orbital steering" or more simply as "steering" in this application. The third oxygen 77, while free to rotate, is constrained to a position that allows its orbitals to align with the "steered" orbitals of the locked oxygens during rotation. This molecule attains a bonding density of approximately 1 bond per 95 daltons, a ratio that compares favorably with the 1 bond per roughly 422 daltons representing the optimum bonding density reported by Sicheri and Yang (see above). The spacing of the locked oxygens 74 and 75 is 4.87 angstroms and the spacing between each locked oxygen and the rotationally free oxygen 77 is 4.58 angstroms.

This particular prototype is chosen for this example also to illustrate the principle of building IIDs that have great structural rigidity to prevent the molecule from flexing and thereby changing the orientation of its ice bonding groups from bonding orientations to non-bonding orientations, as may happen in a simple hexagon, for example when it converts from the "chair" form to the "boat" form or vice versa. The degree of structural control built into the molecule shown in FIG. 7 (IB2) is greater than will often be desirable for easy synthesis, but vividly illustrates the principle of structural control. Compromises between rigidity and function can be made depending upon the requirements of the IID and the costs and practicality of synthesis.

FIG. 8 illustrates a considerably simpler molecule 80 (IB3) that combines less elaborate structural control of one locked oxygen 82 with rotationally permitted alignment on the part of a second oxygen 84. The structure, consisting of three 5-membered rings 85–87 sharing a common pair of bridge carbons 88, could optionally be simplified by deleting the three carbons 89 that form the third, oxygen-free ring 86 which helps to establish the chirality of IB3. As shown, the bonding density is one bond per 84 daltons, and with the three carbon deletion would be one bond per 63 daltons. The oxygen-oxygen separation distance is 4.55 angstroms. In addition, molecules of IB3 can be tethered or rigidly linked together at proper spacings and angles so as to summate bonds over several IB3 monomers for greater overall bonding stability.

FIG. 9 represents a second embodiment of the concepts illustrated in FIG. 8 (IB4). Again, a steered orbital 91 can align with a rotationally free orbital 92 to produce a very local lattice match. The oxygens 93 and 94 are separated by 4.41 angstroms. The bonding density is about one bond per 77 daltons. IB4 monomers can be linked as needed to summate bonds over several monomers as for IB3.

Figure 10:
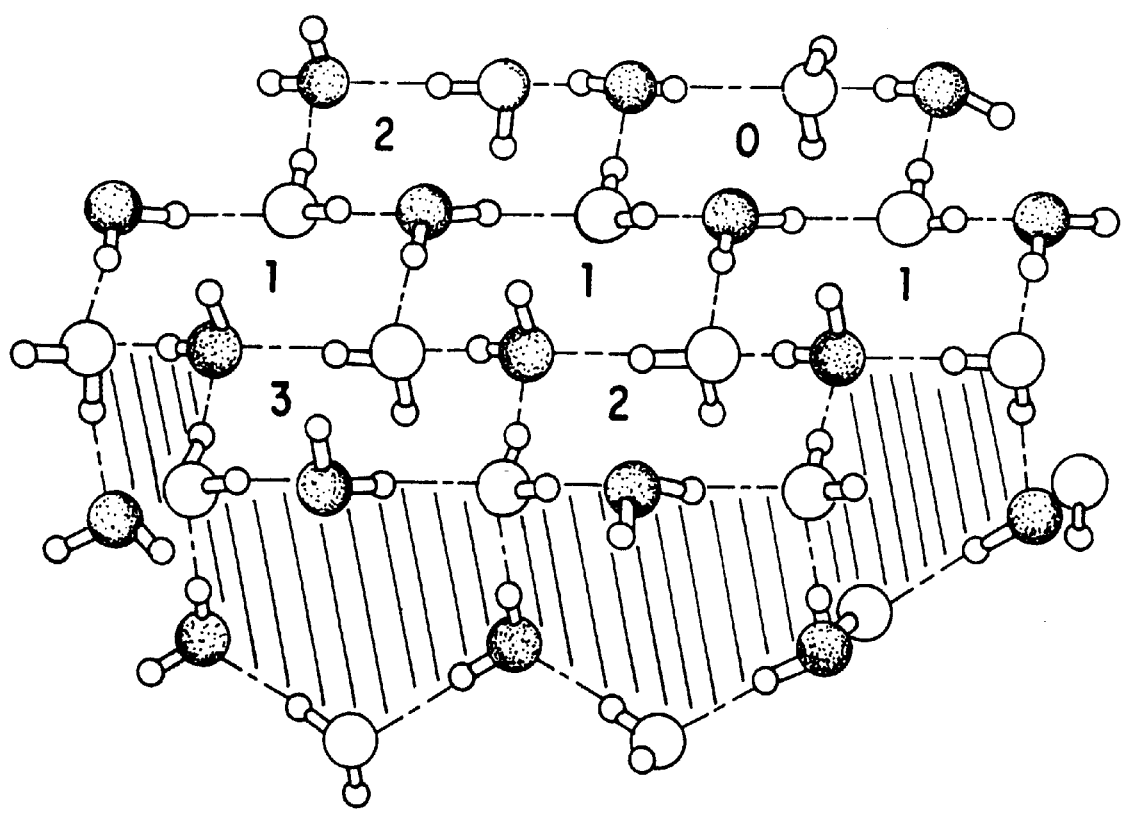
FIG. 10 shows the surface, in atomic detail, of the smallest ice crystal that resembles the macroscopically visible plate-like, hexagonal ice crystal shape.

FIG. 10 represents the simplest aggregation of water molecules that retains the familiar hexagonal plate structure of macroscopically visible ice growing in solution. Water molecules fit into the lattice 100 at random orientations. Thus, on the basal plane 101, the vertical bonds extending upward from the three uppermost atoms of each oxygen hexagon may be three lone pair electron clouds, three hydrogen atoms, two lone pair orbitals and one hydrogen atom, or two hydrogen atoms and one lone pair orbital. From hexagon to hexagon, the distribution of vertical bonds can vary randomly. A specific IID will bond only a fraction of the possible basal plane binding sites that are available, but this is desirable given that complete ice surface coverage is not necessary and that full coating of ice would require more IID than is desirable to incorporate into the solution.

The examples given here are with one exception based on carbon, hydrogen and oxygen only and are devoid of bonds other than single bonds. Clearly, these restrictions are not necessary, but are selected for simplicity and to minimize biological toxicity.

Applications.

The selection of specific IIDs will depend on the particular application at hand, and many applications of IIDs are envisaged.

By preventing Ostwald ripening, IIDs can, for example, prevent frozen foods such as frozen vegetables from sticking firmly together in the household freezer. By reducing the surface energy of ice (the sublimation rate), freezer burn in steaks and other products can be slowed. For such uses, a non-toxic IID can simply be coated on the materials to be frozen.

By preventing coalescence of small ice particles in ice cream and similar products, the storage life of such products can be extended by months, and the ice cream itself will be somewhat softer at household freezer temperature than conventionally produced ice cream without using the enormous sugar concentrations required by the FreezeFlo process, for example. For this purpose, an effective amount of a non-toxic IID can be mixed with the product, preferably before packaging of the product.

By preventing seed crystals from nucleating supercooled water on crops such as citrus crops, thousands of acres of agricultural products (e.g., entire Florida orange groves) can be prevented from freezing on an annual basis, much more reliably and effectively than can be achieved via application of Frostban, a bacterium that simply lacks a nucleating site on its membrane. For this purpose, an IID which is preferably, but not necessarily, non-toxic can be coated on the crops, for example by spraying.

By slowing the growth of ice in vitrifiable solutions of cryoprotective agents, rare ice crystals will remain sufficiently small as to be innocuous to organs, body fluids and other body tissues being vitrified for clinical transplantation or transfusion. For this purpose, an IID which is preferably, but not necessarily, transplantable or transfusable, is added to the tissues, for example by inclusion in a cryoprotective solution.

For preservation by freezing rather than by vitrification, IIDs can be prepared that will be unable to interact directly with nucleating agents, thus allowing a freezing process in which nucleating agents are used to catalyze the formation of large numbers of ice nuclei and the IIDs simultaneously prevent these nuclei from growing to damaging sizes. This will change the physics of ice so as to permit complex systems to survive or to withstand freezing.

IIDs can also be prepared specifically to interact with nucleating substances and thus directly inactivate them to enhance supercooling. This will prevent freezing altogether in many critical applications.

IIDs can also be utilized to stabilize formed ice crystals. For example, they can be used in the snowmaking industry to stabilize previously formed snowflakes to attain a longer-lasting "powder" for skiers' enjoyment. In this application, IIDs can be sprayed onto snow flakes as they are created. This will prevent recrystallization (coalescence) of the snow flakes.

IIDs also have important applications in the prevention of or removal of now-troublesome icing of automobiles, aircraft, rocket boosters, and similar equipment, and in the removal or safe navigation of icing on roadways. They can be incorporated, for example, into the substance and/or treads of tires and shoes so that cars, people and other objects will not slip but will instead actually stick to ice, reducing accidents and injuries due to icy conditions. IIDs can coat thin layers of ice on airplane wings and automobile windshields, presenting a greasy surface that will not stick to additional ice, thereby allowing additional deposited ice to simply be wiped or pushed off or to fall off rather than to be chiseled or melted off.

In these different applications, the non-ice bonding surface of the IID will be modified for ease of assimilation into the substrate material during the manufacturing process, or to achieve goals of solubility, texture suitability or of toxicity limitation. Modifications to the non-ice bonding surface will depend on the substrate material and will be apparent to those skilled in the art. Changes in the ice-bonding surface will be made to extend or reduce the ice adhesion strength in a straightforward manner for the application at hand.

While this invention has been described in conjunction with specific embodiments thereof, it is evident that many alternatives, modifications and variations will be apparent to those skilled in the art. Accordingly, the preferred embodiments of the invention as set forth herein are intended to be illustrative only, and not limiting. Various changes may be made without departing from the spirit and scope of the invention as defined in the following claims.

What is claimed is:

1. A process for preparing an ice interface dopant, comprising, in the stated sequence:
   (1) selecting a substance that nucleates ice, as a template;
   (2) testing whether a non-protein molecule is structurally capable of binding to said template;

(3) if said non-protein molecule proves capable of binding to said template in step (2), testing whether said non-protein molecule inhibits ice crystal growth; and
(4) if said non-protein molecule inhibits ice crystal growth in step (3), identifying said non-protein molecule as an ice interface dopant.

2. A process according to claim 1, further comprising:
(5) bonding a plurality of said non-protein molecules together at edges of said non-protein molecules.

3. A process according to claim 2, wherein step, (5) comprises bonding said non-protein molecules together covalently or by hydrogen bonding.

4. A process according to claim 1, wherein the non-protein molecule for testing in step (2) is selected by:
(a) determining at least one distance between a plurality of ice crystal hydrogen bonding sites on said template; and
(b) selecting a non-protein molecule having at least two dopant hydrogen bonding sites with such a relationship to said distance as to be capable of binding simultaneously with at least two said hydrogen binding sites on said template.

5. A process according to claim 4, wherein said plurality of ice crystal hydrogen bonding sites on said template comprises at least three ice crystal template hydrogen bonding sites.

6. A process according to claim 5, wherein step (2) further comprises determining coordinates of at least three said ice crystal template hydrogen bonding sites, and step (4) comprises synthesizing said non-protein molecule having said dopant hydrogen bonding sites, said dopant hydrogen bonding sites being capable of binding with said at least three ice crystal template hydrogen bonding sites.

7. A process according to claim 6, wherein said dopant hydrogen bonding sites comprise three sites defining triangles being defined by dimensions selected from the group consisting of (i) three sides each 4.5±0.4 Å in length, (ii) three sides each 7.3±0.5 Å in length, and (iii) two sides each 16.7±0.5 Å in length separated by a 48±2° angle.

8. A process according to claim 5, wherein said ice crystal template bonding sites comprise a combination selected from the group consisting of (i) three oxygens, (ii) two oxygens and one hydrogen, (iii) one oxygen and two hydrogens and (iv) three hydrogens.

9. A process according to claim 4, wherein said dopant molecule has a preferentially ice nucleating substance bonding side that contains said non-protein hydrogen bonding sites and a preferentially non-ice nucleating substance bonding side.

10. A process according to claim 9, wherein said preferentially non-ice nucleating substance bonding side does not bind substantially with a preferentially non-ice nucleating substance bonding side of another said non-protein molecule.

11. A process according to claim 4, wherein said at least one distance is selected from the group consisting of 4.5±0.4 Å, 6.3±0.4 Å, 7.3±0.5 Å and 16.7±0.5 Å.

12. A process according to claim 1, wherein said template is an ice crystal.

13. A process according to claim 1, wherein said non-protein molecule comprises at least one hydrogen bonding site fixedly positioned in said non-protein molecule to point a fixed lone pair electron orbital or a hydrogen at one dopant ice crystal template hydrogen bonding site when said non-protein molecule is bound to said template.

14. A process according to claim 13, wherein said non-protein molecule comprises at least two said dopant hydrogen bonding sites fixedly spatially oriented to point lone pair electron orbital(s) at at least two ice crystal template hydrogen(s) bonding sites.

15. A process according to claim 14, wherein said non-protein molecule further comprises a third dopant hydrogen bonding site having a rotatable lone pair electron orbital or hydrogen bond-forming atom so that said third dopant site rotates to point the orbital or the hydrogen bond-forming atom at a third ice crystal template hydrogen bonding site.

16. A process according to claim 13, wherein said non-protein molecule further comprises at least one second non hydrogen bonding site, said second site having a rotatable lone pair electron orbital or hydrogen bond-forming atom, said second site rotating point the rotatable lone pair electron orbital or the hydrogen bond-forming atom to a second ice crystal template hydrogen bonding site when said non-protein molecule is bound to said template.

17. A process according to claim 13, wherein said non-protein molecule further comprises second and third dopant hydrogen bonding sites, said second and third sites each having a lone pair electron orbital or hydrogen bond-forming atom rotatably associated with said fixed lone pair electron orbital so that said second site rotates to point to a second ice crystal template hydrogen bonding site.

18. A process according to claim 13, wherein said non-protein molecule comprises at least three said dopant hydrogen bonding sites fixedly spatially oriented to point lone pair electron orbitals or hydrogen bond-forming hydrogen atoms at at least three ice crystal template hydrogen-bonding sites.

19. A process according to claim 13, further comprising bonding a plurality of said non-protein molecules together at edges of said non-protein molecule.

20. A process according to claim 1, wherein at least a portion of said template matches a basal plane of an ice crystal.

21. A process according to claim 1, wherein the non-protein molecule comprises carbon atoms with attached hydrogen bonding groups physically complementary to hydrogen bonding sites of said template.

22. A process according to claim 1, wherein at least a portion of said template matches a prism face of an ice crystal.

23. The process according to claim 1, wherein computer modeling identifies a substance that nucleates ice. and said substance is selected in step (1).

24. The process according to claim 1, wherein step (2) is performed by computer modeling.

25. A process for identifying an ice interface dopant, comprising, in the stated sequence:
(1) selecting a substance that nucleates ice as a template;
(2) testing whether a non-protein molecule is structurally capable of binding to said template and inhibiting ice crystal growth; and
(3) if said non-protein molecule proves capable of binding to said template in step (2), testing whether said non-protein molecule inhibits ice crystal growth and is thus an ice interface dopant.

26. A process according to claim 25, wherein the non-protein molecule for testing in step (2) is selected by:
(a) determining at least one distance between a plurality of ice crystal hydrogen bonding sites on said template; and (b) selecting a non-protein molecule having a plurality of dopant hydrogen bonding sites with such a relationship to said distance as to be capable of binding to said hydrogen bonding sites on said template.

27. A process for preparing an ice interface dopant, comprising, in the stated sequence;
   (1) providing a substance that nucleates ice, as a template;
   (2) immunizing an animal with said template to cause said animal to produce antibodies that bond to said template;
   (3) collecting said antibodies;
   (4) screening said collected antibodies for antibodies that inhibit ice crystal growth and are thus ice interface dopant antibodies; and
   (5) collecting said ice interface dopant antibodies.

28. A process for preparing an ice interface dopant, comprising, in the stated sequence:
   (1) selecting a substance that nucleates ice, as a template;
   (2) creating by combinatorial chemical synthesis a pool of molecules;
   (3) screening said pool of molecules to collect a subset of molecules that bind to said template; and
   (4) screening said subset of molecules for molecules that inhibit ice crystal growth and are thus ice interface dopants.

29. A process according to claim 28, wherein the dopant molecule comprises polymerized amino acids.

30. A process according to claim 28, wherein the dopant molecule comprises polymerized nucleic acids.

31. A process according to claim 28, wherein the dopant molecule comprises polymerized carbohydrates.

* * * * *